United States Patent [19]

Wegmann

[11] 4,202,815

[45] May 13, 1980

[54] CONCENTRATED POWDER OR GRANULAR FORMULATIONS DISPERSABLE IN AQUEOUS MEDIA

[75] Inventor: Jacques Wegmann, Bettingen, Switzerland

[73] Assignee: Rohner AG Pratteln, Pratteln, Switzerland

[21] Appl. No.: 888,417

[22] Filed: Mar. 20, 1978

[30] Foreign Application Priority Data

Mar. 21, 1977 [CH] Switzerland .......................... 3499/77

[51] Int. Cl.² .................................................. C08K 5/00
[52] U.S. Cl. ...................................... 260/42.21; 8/514; 260/42.43; 260/42.54; 260/42.55; 8/445; 8/512; 8/526
[58] Field of Search ............... 260/42.21, 42.43, 42.54, 260/42.55, 34.2; 8/4; 106/238, 241

[56] References Cited

U.S. PATENT DOCUMENTS

| | | | |
|---|---|---|---|
| 3,844,806 | 10/1974 | Wegmann et al. | 106/241 |
| 3,923,452 | 12/1975 | Wegmann et al. | 8/39 C |
| 3,969,302 | 7/1976 | Wegmann et al. | 260/34.2 |
| 4,001,035 | 1/1977 | Ito et al. | 260/42.21 |

FOREIGN PATENT DOCUMENTS

| | | |
|---|---|---|
| 1108076 | 4/1968 | United Kingdom . |
| 1160712 | 8/1969 | United Kingdom . |
| 1178846 | 1/1970 | United Kingdom . |
| 1203558 | 8/1970 | United Kingdom . |
| 1238118 | 7/1971 | United Kingdom . |
| 1474112 | 5/1977 | United Kingdom . |
| 1491736 | 11/1977 | United Kingdom . |

*Primary Examiner*—Lewis T. Jacobs
*Attorney, Agent, or Firm*—Finnegan, Henderson, Farabow, Garrett & Dunner

[57] ABSTRACT

Process for the preparation of concentrated formulations, which can be dispersed in aqueous media, in the form of free-flowing, low-dusting powders or granules starting from active substances which are sparingly soluble to insoluble in water, such as pigments, dyestuffs, optical brighteners, and other related types of additives.

15 Claims, No Drawings

CONCENTRATED POWDER OR GRANULAR FORMULATIONS DISPERSABLE IN AQUEOUS MEDIA

DESCRIPTION

The present invention relates to a process for the preparation of concentrated formulations, which can be dispersed in aqueous media, in the form of free-flowing, low-dusting powders or granules starting from active substances which are sparingly soluble to insoluble in water, such as pigments, dyestuffs, optical brighteners, plastics additives, textile auxiliaries, textile finishing agents, insecticides, herbicides, pharmaceuticals and other related types of active substances, and to the use of these formulations for the preparation of aqueous dispersions having the most diverse concentrations.

The principle of the process according to the invention is in itself known, and the application of this principle to the preparation of formulations consisting of water-insoluble dyestuffs or pigments and water-insoluble carrier resins is described in detail in Swiss patent specification No. 536,341, No. 560,234 and No. 565,210; the formulations prepared according to this Swiss patent specification are intended for use in organic media, such as melts and solutions. In Swiss patent specification No. 557,413, the process has been expanded, and extended to the preparation of formulations which can be dispersed in aqueous media and which contain water-soluble carrier resins, such as, for example, polyvinyl alcohol, hydroxypropylcellulose and carboxymethylcellulose. According to Swiss patent specification No. 557,413, carrier resins can be used which are soluble in one of the two phases of the two-phase system but are insoluble in the two-phase system itself. To be exact, the carrier resins must be "essentially undissolved" in the two-phase system, which is a matter of proportions. However, it is much more difficult to prepare formulations which can be easily dispersed in aqueous media with carrier resins of this type which are soluble in the aqueous phase than to prepare formulations which can be easily dispersed in organic media with carrier resins of this type which are insoluble in the aqueous phase. Apart from the fact that the carrier resins which are soluble in the aqueous phase display only a weak dispersing action in an aqueous medium, this difficulty is probably due to the fact that if carrier resins which are soluble in the aqueous phase are used, it is not possible to decrease the volume of the organic phase of the two-phase system, which contains the dyestuff and the carrier resin, by adding further water in order to isolate the formulation; rather, the solvent must be distilled off or evaporated together with the water in order to avoid high losses of carrier resin as a result of the transfer of the carrier resin into the aqueous phase. However, the redispersibility of the formulations is thereby impaired, so that these have poorer properties than the formulations which can be dispersed in aqueous media and are prepared according to the state of the art by spray drying or freeze drying. For dispersing formulations containing active substances in organic media, it is customary to use intensive stirrers and similar special equipment and to accept long stirring times of up to one hour. However, it should be possible to easily, rapidly and completely disperse formulations which can be dispersed in aqueous media, by simply stirring them into water.

It has now been found that very concentrated, solid formulations, which can be easily and completely dispersed in aqueous media, of active substances which are sparingly soluble to insoluble in water can be prepared according to the invention if high-molecular organic substances which are sparingly soluble to insoluble in water, contain acid groups and can be converted into a water-soluble form with bases are used as the carrier resins.

The process according to the invention is characterised in that at least one active substance which is sparingly soluble to insoluble in water is distributed in the organic phase of a two-phase system consisting of water, which optionally contains electrolytes, and an organic solvent which has a limited solubility in the aqueous phase, preferably a solubility of at least 1% by weight, but in particular more than 10% by weight, the two-phase system, which contains the active substance or the active substances in very fine dispersion, preferably with an average particle size of less than 2 microns, in the organic phase and has a liquid to paste-like consistency, is treated, with thorough turbulent mixing, with high-molecular organic carrier substances which are sparingly soluble to insoluble in water, contain acid groups and can be converted into a water-soluble form with bases, until a homogeneous mixture has been obtained, the volume of the organic phase, which contains the active substance or the active substances and the carrier substance, is reduced by adding further water, as a rule whilst stirring, until the formulation particles formed are no longer sticky and can be easily separated off, for example by filtering or decanting, and the particles which have been separated off are freed from solvent residues and impurities by rinsing with water and are optionally dried; however, after rinsing with water, the particles which have been separated off can also be stirred directly into an aqueous medium under conditions under which the carrier substance is readily soluble, in order to prepare a concentrated dispersion of the active substance or of the active substances.

According to the Patent Claim of Swiss patent specification No. 557,413, the carrier resin may be added only after the two-phase system has formed; this is not necessary in the process according to the invention. On the contrary, the reduction in the volume of the organic phase by adding further water so that further organic solvent is taken up by the aqueous phase is an essential characteristic of the process according to the invention and is important with respect to the quality of the formulations prepared according to the invention.

The formulations, prepared according to the invention, of active substances which are sparingly soluble to insoluble in water have a number of advantages which are as remarkable as they are surprising. They can be dispersed rapidly and completely in aqueous media by simply stirring them in, with the addition of bases, preferably amines, stable dispersions being obtained. Concentrated stock dispersions which can be further diluted or dilute dispersions having a concentration suitable for the desired use can be prepared in this manner. In spite of this, the formulations need contain only a minimal amount of the carrier substance, which as a rule is between 10 and 50% by weight. Moreover, the carrier substance is readily biologically degradable, free from undesired side effects and inexpensive. A further advantage which may be mentioned is that the formulations prepared according to the invention are obtained in the form of stable, free-flowing, non-dusting powders or granules, the particle sizes of which can be essentially adapted to the particular requirements by suitably choosing the process conditions. As a rule it is not necessary to comminute the formulations further using a centrifugal mill (dismembrator) or to sieve them. They are obtained in a fine-particled form which is easy to handle and can be easily dispersed.

A process for the preparation of fine-particled granules has already been disclosed, namely two-phase granulation. Two-phase granulation is understood as the conversion of a finely powdered substance into granules by stirring in a two-phase system, which can be carried out by two fundamentally different procedures. The powder to be granulated is either stirred into an organic solvent which is not water-miscible to an unlimited extent, and small amounts of water are added as the granulating agent, or the powder to be granulated is dispersed in water and an organic solvent which forms a second phase with water is added as the granulating agent. The first variant is described, for example, in Canadian Journal of Chemistry 38, 1911 (1960) and is suitable for hydrophilic or water-soluble substances. The second variant is suitable for organophilic, water-insoluble substances and has been described in German Auslegeschriften No. 1,256,644, No. 1,279,658, No. 1,669,783 and No. 1,768,199 and U.S. Pat. No. 3,755,244. The latter type of granulation also occurs in the process according to the invention. It therefore seems appropriate to go into this process in more detail in order to distinguish the present invention from the above-mentioned state of the art.

The wet granulation in a two-phase system differs from the process according to the invention, which for simplicity is to be designated "two-phase formulating process", in that, inter alia, only about 10 to 20% by weight of organic phase used as the granulating agent, relative to the substance to be granulated, are used in the two-phase granulating process and the organic phase remains in the finished formulation. If an additional volatile solvent is used in the two-phase granulating process, this also remains in the finished formulation, from which it can be removed only by distillation. Furthermore, solvents which are insoluble in water, or only traces of which dissolve in water, must be used in the two-phase granulating process; in addition, no carrier substances are used. Binders which serve to increase the stability of the granules formed to exposure to mechanical load and to lower their tendency to disintegrate with the formation of fine, dusting constituents can, but do not have to, be used in the two-phase granulating process.

A further process for the preparation of non-dusting granules which are readily wettable and can be rapidly dispersed has recently been described in German Offenlegungsschrift No. 2,412,369 of Mar. 16, 1973 (compare also German Offenlegungsschrift No. 2,459,457), which combines both the variants described above of the two-phase granulating process and is said to be suitable both for granulating water-soluble substances and for granulating water-insoluble substances. Surprisingly, the granules prepared according to German Offenlegungsschrift No. 2,412,369 are said to be distinguished by so-called "instant" properties, that is to say they are said to disperse or dissolve instantaneously and completely. Where the statements in this German Offenlegungsschrift relate to the granulation of active substances which are sparingly soluble to insoluble in water, they have been examined carefully, since if they were true they would make the present invention superfluous because the results of the process according to the invention would be poorer than those of the process according to the German Offenlegungsschrift. The formulations prepared according to the German Offenlegungsschrift are, in fact, free from carrier substances, for which reason they would have to have the advantage of universal applicability. Furthermore, they can supposedly be dispersed not only in aqueous media but also in organic media. Where the statements of the German Offenlegungsschrift could be examined with the aid of embodiment examples which relate to substances which are sparingly soluble to insoluble in water (for example Examples 5/4 and 10), they could not be confirmed. The granules prepared according to these examples can be neither wetted easily nor dispersed rapidly and in addition they cannot be dispersed at all in an aqueous medium. Furthermore, they are also not stable to exposure to mechanical loads and disintegrate into a fine, dusting powder even when shaken slightly in a bottle. In the introduction of German Offenlegunsschrift No. 2,412,369, additional statements are certainly made which are not contained in the examples. It is mentioned, for example, that particularly good results are obtained by grinding the dispersion of the active compound before granulating, and that binders, such as polyvinyl alcohol, hydroxypropylcellulose or polyvinylpyrrolidone can be added. Comparison experiments were therefore carried out in which in each case half of a dispersion of active compound was worked up, after grinding and adding a binder, by wet granulation according to the statements in the German Offenlegungsschrift or by spray drying. In contrast to the statements in the introduction of the German Offenlegungsschrift, the formulations obtained by spray drying could be dispersed better and more rapidly in water than the granules prepared by wet granulation according to the German Offenlegungsschrift. Where it can be examined by the expert, on the basis of the statements in the German Offenlegungsschrift, the formulations obtainable according to this German Offenlegungsschrift thus have considerably poorer properties than the formulations obtainable according to the invention.

Formulations obtained in the above comparison experiments which have been spray-dried and contain only 5% by weight of binder certainly always have even poorer properties than the best formulations according to the state of the art. In order to be really perfectly redispersible, they must contain 50 to 70% by weight, depending on the active substance used, of a carrier material or dispersing agent which is readily soluble in water. In addition, formulations which have been spray-dried are very voluminous and dust severely. They can indeed be rendered non-dusting by finely spraying with an oil formulation, but this is again associated with other disadvantages. In additon to this is the fact that the best dispersing agents which can be used for such formulations have a number of adverse side effects. The most widely known and best diluents having a good dispersing action are purified sulphite cellulose waste liquor products, condensation products of naphthalenesulphonic acids and formaldehyde as well as condensation products of ethylene oxide and fatty alcohols or phenols, or mixtures of such products. However, these diluents have a number of troublesome side effects in aqueous media, especially if they are present in relatively high concentrations, which cannot always be completely removed by adding agents having an opposite action. In textile finishing, for example, these diluents promote the migration of the active substances, hinder the absorption of dyestuffs from a dyebath, cause foam formation and, because of their poor biological degradability, lead to ecological problems.

Active substances which are sparingly soluble to insoluble in water, are suitable for use in very fine dispersion in aqueous media and are particularly advantageously used in the form of the solid formulations obtainable according to the invention which can be easily dispersed, contain physiologically and ecologically acceptable carrier substances and are free from water-soluble dispersing agents are found in a large number of classes of compounds. Examples of such active compounds are insecticides, herbicides, flameproofing agents, antioxidants, stabilisers, cosmetics and pharmaceuticals, and especially naturally occurring dyestuffs, such as carotinoids, synthetic dyestuffs or dyestuff precursors, such as deprotonated basic dyestuffs, mordant dyestuffs, solvent dyestuffs, metal complex deystuffs, disperse dyestuffs, naphthol dyestuffs and vat dyestuffs, but very particularly inorganic and organic pigments. Inorganic pigments which may be mentioned are: carbon black, titanium dioxide, iron oxide hydrates, various metal powders, chromium oxide and ultramarine, and organic pigments which may be mentioned are those from the class comprising the azo, anthraquinone, phthalocyanine, nitro, perinone, perylenetetracarboxylic acid diimide, dioxazine, indolinone, imidazole, quinacridone, indigo and thioindigo series.

The active substances should appropriately be in as fine as possible division, suitable for the particular intended use, in the organic phase for the treatment with the carrier substance; this fine division can be achieved by mechanical or "chemical" comminution. Mechanical comminution by wet grinding in a ball mill, sand mill or roll mill in the solvent phase or in water is preferred, because a regular and controllable fine division is thereby achieved. This is particularly important if the degree of action of the active substance depends on the particle size and must be standardised with regard to certain requirements. If the grinding or the "chemical" comminution (for example by reprecipitation) is carried out in water, the active substance must be transferred as completely as possible from the aqueous into the organic phase before the treatment with the carrier substance. This so-called flushing operation usually proceeds spontaneously. If this is not the case, flushing auxilaries must be used. Howver, it is better to ensure that no auxiliaries which interfere with the flushing operation or the formation of a two-phase system are present during grinding. If this is not possible, the active substance should be ground in the organic phase and not in the aqueous phase. However, under no circumstances may other synthetic resins which are only soluble in organic media be present during grinding in the organic phase, since non-uniform formulations which in addition are poorly dispersible, or cannot be dispersed at all, in an aqueous medium would be obtained if such synthetic resins are present.

Examples of high-molecular organic carrier substances, which can be used according to the invention, which are sparingly soluble to insoluble in water, contain acid groups and can be converted into a water-soluble form with bases, such as alkalis, ammonia or amines, are the resin acids, that is to say naturally occurring or synthetic resins which contain one or more acid groups in the molecule and are described, for example, in "Karstens Lackrohstofftabellen" ("Karstens Lacquer Raw Material Tables"), 5th edition, Vincenzverlag, Hanover. Numerous other suitble carrier substances are also listed there, such as, for example, alkyd resins, for example acid phthalate resins, as well as resin acid derivatives. Particularly good results are obtained with reaction products of maleic acid and resin acids, or copolymers of maleic acid and similar unsaturated acids or their anhydrides or esters with olefines, such as ethylene, propylene, butylene or diisobutylene, vinyl esters, vinyl ethers, vinyl chloride or other unsaturated compounds. Copolymers of styrene and maleic acid or derivatives thereof are particularly suitable. The carrier substances must be high-molecular, that is to say they must have, as a rule, a molecular weight of over 500, preferably over 1,000. Carrier substances having molecular weights of over 50,000 are nevertheless generally undesired, since if such carrier substances are used, formulations would be obtained, the dispersions of which in an aqueous medium would have too high a viscosity. It is very important that, in their water-soluble form, the carrier substances can be easily and rapidly dissolved in an aqueous medium. In addition to alkalis, such as sodium hydroxide or sodium carbonate, above all volatile amino compounds, such as ammonia and alkylamines, but also arylamines, are suitable for converting the carrier substances into a water-soluble form.

Whether highly volatile bases are used for converting the carrier substance into a water-soluble form depends, above all, on the intended use of the dispersions which are to be prepared from the formulations.

For the treatment of the active substance or of the active substances with the carrier substance to proceed well and smoothly, it is important that the carrier substances are in a form which is sparingly soluble to insoluble in water and that the aqueous phase of the two-phase system contains no additives, such as basic substances, which render the carrier substance water-soluble.

In certain cases, the carrier substance can have a similar action to the active substance or an action which complements the action of the active substance. The carrier substances can themselves have, for example, bactericidal, insecticidal, herbicidal or fungicidal properties. On the other hand, in the case of formulations for cosmetic or pharmaceutical purposes, carrier substances which as far as possible are inert, can be readily degraded biologically and cause no allergic reactions will be preferred. Examples of such carrier substances are reaction products of resin acids with maleic acid and polyols, as well as certain styrene/maleate resins.

Solid formulations of active substances, such as, for example, solid pigment formulations, which contain the same constituents as the formulations obtainable according to the invention and their preparation, although by a completely different process, have already been described. However, as a result of their preparation in a completely different manner, these known formulations also have completely different properties. In particular, pigment formulations containing acid resins have already been frequently proposed. Examples of such formulations are the pigments treated in accordance with the resination process, which are known from U.S. Pat. No. 3,159,498, Japanese patent specification No. 48/91,127 and German Auslegeschrift No. 1,767,245. The process described in these patent specifications proceeds in a diametrically opposite manner to the process according to the invention and also pursues the exact opposite aim. In fact, by the process of the patent specifications mentioned, the pigment particles are dispersed in an aqueous solution of a salt of a resin acid and are coated with a thin, film-like resin acid layer by precipitating the water-insoluble resin acid with the aid of an acid. The so-called resinated pigments obtained in this manner, the surface properties of which have been changed by the resin coating, show an improved affinity to organic media and are distinguished by a more ready dispersibility in organic solutions or melts. A relatively thin resin coating of 5 to 10% by weight, relative to the pigment, is sufficient to achieve this effect. In individual cases an improvement in the dispersibility in aqueous media is also achieved by the resination; in the case of disperse dyestuffs having too high a water-solubility, it has been proposed, for example in German Auslegeschrift No. 2,100,439, to lower the water solubility by resination. Resinated dyestuffs of this type can furthermore be converted into dyestuff formulations by known methods using known dispersing agents.

In addition to formulations which contain simple, optionally dimerised resin acids, such as abietic acid or colophonium (which are customarily used for the resination of pigment and which are not particularly suitable for use in the process according to the invention), pigment formulations have also already been described which contain copolymers of maleic acid or derivatives thereof and olefinically unsaturated compounds, especially also styrene, which are more suitable for the process according to the invention. Thus, solid mixtures of pigments containing a copolymer of styrene and a maleic acid half-ester which are prepared by mixing the finely powdered components are known, for example, from British patent specification No. 717,838. Similar pigment formulations which contain copolymers of aliphatic olefines and maleic acid and are prepared by dry grinding of the components are described in U.S. Pat. No. 3,000,840. The formulations in the latter two patent specifications are indeed solid formulations, but in contrast to the formulations prepared according to the invention, these cannot be dispersed in water by means of simple stirring. Pulverulent formulations which contain styrene/maleate resins and can be used in organic media have been described in British patent specification No. 1,329,652. The preferred process for the preparation of formulations which contain styrene/maleate resins of low molecular weight, that is to say those with a molecular weight of 1,000 to 2,000, is, according to the statements in various patent specifications, the so-called solvent/salt kneader process in which the components are treated in a kneader in the presence of salt and a solvent. German patent specification No. 1,469,724 describes the preparation by this process of formulations for use in an organic medium and British patent specification No. 1,311,185 describes the preparation by this process of formulations for use in an aqueous medium.

Compared with the process according to the invention, the solvent/salt kneader process has a number of important disadvantages in the preparation of formulations which can be dispersed in an aqueous medium. By the solvent/salt kneader process, formulations can be prepared which are not as concentrated and cannot be dispersed as readily as those prepared by the process according to the invention. The solvent/salt kneader process also requires a considerably higher expenditure on apparatus and energy than the process according to the invention and is associated with much more difficult ecological problems. It is possible to prepare by the process according to the invention not only formulations which, as the above-mentioned known formulations which are prepared by the solvent/salt kneader process, contain styrene/maleate resins having a molecular weight of 1,000 to 2,000, but also highly concentrated formulations which can be very readily redispersed and contain highly polymeric styrene/maleate resins having molecular weights of over 20,000. On the basis of statements in earlier patent documents than those cited above, the view was hitherto taken that the highly polymeric copolymers mentioned have dispersing properties which are not as good as the corresponding low-molecular copolymers. The formulations which contain as carrier substances highly polymeric styrene/maleate resins having molecular weights of over 20,000 are new. They need contain only 10 to 30% by weight of carrier substance, that is to say they can have particularly high concentrations of active substance, and when amines are added give particularly stable aqueous dispersions. They can also contain a small amount of a maleate polymer or copolymer having a low molecular weight of 1,000 to 2,000 as an additive in order, for example, to adapt the viscosity properties to the particular requirements.

The carrier substances must be sparingly soluble to insoluble in water and it should be possible to convert them easily and rapidly into a completely water-soluble form at room temperature with the aid of bases which can be dispersed rapidly and easily. It is therefore very important that they are not contaminated with other synthetic resins, such as, for example, ethylcellulose, which cannot be converted into a water-soluble form with bases. Such synthetic resins can, of course, also be introduced into the formulation via the organic phase in the course of the process. Grinding additives which are exclusively soluble in the organic phase should therefore not be used.

When the four components required for carrying out the process according to the invention, namely the aqueous phase, the organic phase, the dissolved or dispersed carrier substance and the dispersed active substance or the dispersed active substances, have been brought together, essentially in any desired sequence, it must be ensured, by thorough turbulent mixing, for example by intensive stirring or also shaking, that both the carrier substance and the active substance, or the active substances, are transferred completely into the organic phase of the two-phase system. The volume of the organic phase must be sufficiently large for it to be able to take up the carrier substance and the active substance or the active substances and nevertheless still remain liquid enough for homogeneous thorough mixing to be possible. The carrier substance must be present in a form which is sparingly soluble to insoluble in water so that it is transferred to the organic phase; thus the aqueous phase may not contain constituents which render the carrier substance water-soluble. If necessary, the carrier substance can be precipitated completely, for example by adding acid. As soon as homogeneous mixing of the active substance or the active substances and the carrier substance in the organic phase has been achieved and the aqueous phase is free from these substances, the reduction in the volume of the organic phase can be started by adding further water. As a rule, water is added, whilst stirring vigorously, in an amount such that some of the second phase still remains, after which the system is stirred until the aqueous phase is saturated with the solvent and the formulation has disintegrated to give granules with the desired particle size. In certain circumstances, this can be achieved by wet comminution, for example using a Turmix ® domestic mixer (with a rotating ring of cutters) or apparatuses having a similar action. The aqueous phase, which has been almost saturated with solvent, can now be filtered off and the solvent can be regenerated by azeotropic distillation. For rapid removal of solvent residues, the formulation can be stirred in fresh water for some time, filtered off on a suction filter, washed with water and then dried. All the operations, with the exception of the drying, are preferably carried out at room temperature.

The amount of carrier substance chosen is preferably as low as possible. It is possible to prepare formulations which contain 20 to 90% by weight, preferably 40 to 70% by weight, of active substance or active substances. The minimum amount of carrier substance which is required in order to ensure complete redispersibility of the formulation depends, above all, on the degree of fineness of the active substance or the active substances.

According to a particular embodiment of the process according to the invention, a water-insoluble active substance is comminuted in an aqueous medium together with the carrier substance or a portion thereof, for example by grinding, reprecipitating or a combination of these measures. In most cases, the active substance can already be sufficiently finely dispersed by reprecipitation, so that no additional grinding is required. If the carrier substance or a small portion thereof is present during the grinding in water, this should be converted into a water-soluble form. After grinding, it can be appropriately reprecipitated from the aqueous phase so that it passes into the organic phase of the two-phase system. Maleate polymers and copolymers having a molecular weight of less than 20,000, preferably between 1,000 and 2,000, are particularly suitable for this embodiment.

Suitable organic solvents which have a limited solubility in the aqueous phase are all the polar solvents which display a so-called miscibility gap with water so that they form a two-phase system when mixed with water. For economical reasons, the solubility of the organic solvent in water should be as high as possible and is preferably 10 g/liter, but in particular 100 g/liter, since after the treatment with the carrier substance the two-phase system must be essentially converted, by further addition of water, into a single-phase system, the volume of which is larger the lower the solubility of the organic solvent in water. It must be taken into consideration that in the case of a solubility of only 10 g/liter, ten times as much solvent/water mixture must be regenerated by distillation than in the case of a solubility of 100 g/liter. An organic solvent having a low solubility in water is thus only used if this is absolutely necessary for industrial reasons. For the same reasons, it is also advantageous if the active substance is present in as high as possible a concentration during grinding.

Examples of suitable solvents are chlorinated hydrocarbons, such as methylene chloride, nitriles, such as acrylonitrile, nitro compounds, such as nitromethane, aldehydes, such as furfural, ethers, such as 2-phenoxyethanol, esters, such as ethyl acetate and ketones, such as methyl ethyl ketone or 4-methoxy-4-methyl-2-pentanone, but in particular alcohols, such as n-butanol, sec.-butanol or isobutanol, and also propylene carbonate and mixed ether-ester compounds, such as 2-ethoxyethyl acetate. It is also possible to use those solvents which have a limited solubility, and form a two-phase system, in electrolyte-containing water, such as, for example, tert.-butanol, diacetone-alcohol, ethylene carbonate, acetonylacetone or hydroxyacetone. In such cases, the formation of the second, that is to say the organic, phase is brought about by a content of electrolytes, such as sodium chloride, in the aqueous phase.

In no case can solvent be saved by grinding the active substance or the active substances in water. The active substance or the active substances must, in fact, be completely dispersed in the organic phase in the perfect, stable deflocculated state during the treatment with the carrier substance. This means that the concentration of the active substance or the active substances in the organic phase cannot be higher than if grinding had been carried out in an organic solvent. In the case of grinding in an organic solvent, the concentration of the active substance or the active substances may as a rule be at most 50% by weight. The volume of the organic phase must thus as a rule be at least the same as the volume of the active substance or the active substances.

The solid formulations according to the invention are intended for use in the form of aqueous dispersions. They can be most simply converted into an aqueous dispersion by being stirred or sprinkled into an aqueous medium which contains the bases required for converting the carrier substance into a water-soluble form. Thickeners can be added beforehand or afterwards. As a rule, it is more advantageous to prepare a concentrated dispersion of the formulation and then to dilute this as required, because the carrier substance dissolves in the aqueous medium more rapidly at a higher base concentration, no substantial excess over the stoichiometric amount of the base being required. However, it is also possible to introduce a formulation according to the invention into a vessel and to pour over the optionally thickened aqueous medium containing a base. Intensive stirring is not necessary. It is possible, but as a rule not necessary, to predisperse the formulations according to the invention in alcohol and then to stir the alcoholic dispersion into the aqueous medium. Bases which can be used are aqueous alkalis, but especially bases which are readily soluble in water, such as ammonia or amines, such as, for example, ethanolamines, morpholine or hexamethylenediamine.

The formulations according to the invention can be stirred directly into aqueous application media which already contain bases, such as vat dyebaths, naphthol impregnation baths or spinning solutions for the preparation of viscose fibres or cuprammonium rayon. It is nevertheless also possible to first convert the vat dyestuff formulations or pigment formulations used for this purpose into an aqueous stock dispersion and to add this to the application media.

As a rule, the carrier substance contained in the formulations according to the invention is not adequate as a film-forming agent and thickener for printing onto temporary supports for heat transfer printing, such as paper webs, plastic films or metal foils, or for direct printing onto textiles or paper. In choosing additional thickeners it must be taken into consideration that they should be either anionic, as the carrier substances, or non-ionic.

The formulations according to the invention can be combination formulations which contain several active substances of a different type, for example disperse dyestuffs and vat dyestuffs or dyestuffs and finishing agents. Since the carrier substances contain reactive acid groups, crosslinking agents can also be added to the formulations, for example in order to achieve additional fixing and stabilising of the prints in pigment printing. Because of their low concentration in the formulations and their low viscosity, the carrier substances scarcely change the properties of the textiles treated and therefore do not need to be washed out. In the case of exhaustion dyeings, of course, they remain in the dyebath, since they have no affinity for textiles. Since they can be precipitated with acids, in contrast to the removal of the water-soluble dispersing agents which were hitherto customary, their removal from the effluent presents no difficulties. This is of considerable importance not only in the case of the dyeing of textiles, but also, especially, in the case of beaten dyeing of paper, where large amounts of effluent result.

It is very particularly advantageous, in the case of dyeing with vat dyestuffs and disperse dyestuffs by padding and thermofixing and/or steam, that the formulations according to the invention contain no water-soluble dispersing agents at all, because no undesired and uncontrollable migration of the dyestuff occurs, the degree of fixing of the dyestuff is not decreased and the after-treatment operations can be confined to a minimum and carried out with small amounts of water. The formulations according to the invention are also ideally suitable for combined dyeing and finishing processes by padding and drying, which are preferred at present, since no by-products need to be washed out.

The dyestuff formulations and pigment formulations according to the invention, optionally after adding further fixing agents or finishing agents, are very particularly suitable for textiles which have no affinity for certain groups of dyestuffs, such as textiles made of glass, asbestos, polypropylene or aromatic polyamides, such as, for example, Nomex ® (Du Pont).

The examples which follow illustrate the invention. Parts are parts by weight and temperatures are indicated in °C.

EXAMPLE 1

100 Parts of a 40% strength aqueous press cake of 2-hydroxy-anthracene-3-carboxylic acid o-toluidide are stirred with 10 parts of a styrene/maleate resin, commercially available under the name SMAC A (van Baerle) in 100 parts of methyl ethyl ketone saturated with water. The mixture is then diluted gradually with water, whilst continuing intensive stirring, until the formulation disintegrates into fine granules. The aqueous phase is then filtered off, the product is twice covered with fresh water and the formulation particles are suction-drained, rinsed with water and dried in a vacuum cabinet at 60°. The formulation obtained is free-flowing and easy to handle, does not dust and can be dispersed rapidly and completely in an alkaline medium. Dispersions prepared in this way are suitable for naphtholating textiles, such as, for example, cotton fabrics.

If instead of methyl ethyl ketone acetylacetone, 4-methoxy-4-methyl-2-pentanone or propylene carbonate are used and in other respects the procedure described above is followed, or if acetonylacetone, diacetone-alcohol or ethylene carbonate are used and 10% by weight of sodium chloride are also added to the aqueous phase, but in other respects the procedure described above is followed, comparably good results are obtained.

EXAMPLE 2

100 Parts of an aqueous press cake of 4-nitro-2-methoxyaniline containing 40% of solids are ground in the presence of 1 part of a dinaphthylmethanedisulphonate, commercially available under the name Lomar ® D (Nopco), by means of 200 parts of glass beads of 1 mm diameter, until a particle size of less than 1 micron is reached. After removing the glass beads, 100 parts of sec.-butanol saturated with water and 10 parts of a maleate resin commercially available under the name Hercules Resin B 106 (Hercules) are added. After thoroughly stirring and homogenising the mixture, the latter is slowly diluted with water until a finely granular formulation has been formed. The supernatent aqueous phase is then filtered off, and the product is covered twice with fresh water, suction-drained, washed and dried. A free-flowing, non-dusting formulation which can be easily and completely dispersed in an alkaline medium, is obtained; it can be diazotised in accordance with customary processes and used together with naphthol derivatives, such as that mentioned in Example 1, for dyeing or printing of textiles.

If instead of the abovementioned aniline the same amounts of 1-amino-2,5-dimethoxy-azobenzene or 1-amino-2,5-dimethoxy-4-benzoylaminobenzene are used and in other respects the procedure described is followed, comparably good formulations are obtained. If the maleate resin mentioned in the above example is replaced by the same amounts of SMA 2625 A (Arco Chemical) or Alresat ® KM 444 (Reichhold-Albert), good formulations are again obtained.

EXAMPLE 3

20 Parts of the naphthol of the formula:

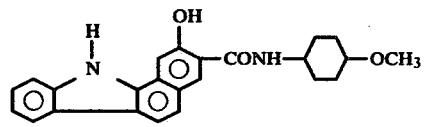

in 80 parts of sec.-butanol which has been saturated with water are stirred intensively, with addition of 2 parts of a maleate resin and 1 part of sodium hydroxide, until homogeneous distribution is achieved. Dilute aqueous sulphuric acid is then added gradually, with continued stirring, until the formulation which separates out has assumed the desired finely granular form. The aqueous phase is then filtered off and the product is covered three times with fresh water, suction-drained, washed and dried.

EXAMPLE 4

20 Parts of 3-(p-chloroanilino)-10-(p-chlorophenyl)-2,10-dihydro-2-(isopropylimino)-phenazine (Clofazimin) are ground in the presence of 1 part of dinaphthyl-methanedisulphonate in a sand mill until the particle size is essentially below 1 micron. After separating off the grinding auxiliary and filtering the dispersion through a 5 micron filter, 5 parts of a styrene/maleate resin having a mean molecular weight above 30,000, in 100 parts of methyl ethyl ketone saturated with water, are added to the dispersion, with intensive stirring. Thereafter, water is added, with continued stirring, until the initially pasty organic phase disintegrates into individual particles. The aqueous phase is filtered off and the formulation is covered three times with fresh water, washed thoroughly with water on the suction filter, and dried. This gives free-flowing, easily handled and non-dusting granules which can be easily and completely dispersed in an aqueous medium, with addition of ammonia or water-soluble amines, to give an extremely fine and stable dispersion. This dispersion can be used for pharmaceutical purposes, especially for the treatment of leprosy (see Basler Nachrichten No. 251 of June 20, 1969).

EXAMPLE 5

20 Parts of 2,5-di-[benzoxazolyl-(2')]-thiophene are milled in a ball mill, with addition of 1 part of a dinaphthylmethanedisulphonate in 80 parts of water, until the particle size is less than 1 micron. The dispersion is separated off, stirred with 10 parts of a maleate resin in 100 parts of sec.-butanol saturated with water, and diluted with water until a fine granular material is formed. The aqueous phase is filtered off and the formulation is covered twice with fresh water, suction-drained, washed and dried. The formulation obtained can be stirred into an aqueous medium, with addition of bases, especially ammonia, to give an extremely fine dispersion. It is used for the optical brightening of textiles and can, for example, be added to detergents.

EXAMPLE 6

500 Parts of a dried press cake of 1-amino-2-chloro-4-hydroxyanthraquionone are introduced slowly, with good stirring, into 500 parts of a 2% strength solution of Tamol® NNOK (a condensation product of naphthalenesulphonic acid and formaldehyde from BASF or Rohm & Haas). This slurry is then ground in a Dynomuhle®, type KDL (Bachofen, Basel), with glass beads of 1 mm diameter as grinding bodies, by pumping the slurry to and fro between two vessels, until the dispersion no longer contains any particles larger than 5 microns. The pigment content is brought to 40% by weight by dilution with water, after which the dispersion is filtered.

A solution of 13.3 parts of a maleate resin, commercially available under the name Hercules Resin B 106 (Hercules), in 80 parts of sec.-butanol saturated with water, is now added to 100 parts of the above dispersion, whilst stirring with a toothed-disc stirrer, and the mixture is stirred, with addition of a further 10 parts of sec.-butanol, until the aqueous phase which has separated out appears colorless.

The mixture is then diluted slowly, with intensive stirring, with a further 300 parts of water, the supernatent aqueous phase is filtered off, the granules formed are slowly stirred for one hour after making up with water to the same volume as before, and the product is then filtered off on a suction filter carrying a cotton filter pad, washed repeatedly with fresh water and then dried in a vacuum drying cabinet at 60°. The formulation obtained consists of free-flowing, non- dusting granules of size about 1 mm.

5 Parts of the formulation are stirred into 20 parts of a mixture of 15 parts of water and 5 parts of concentrated ammonia; the stock dispersion thus obtained is then mixed with 25 parts of a 4% strength aqueous sodium alginate solution. A paper is screen-printed with the printing ink thus obtained, the printed paper is dried and the print is transferred from the paper to a polyester fabric by pressing in an ironing press for 30 seconds at 200°. A good red print is obtained.

10 parts of the formulation are dispersed in the course of 10 minutes in 90 parts of an 8% strength solution of ethylcellulose in ethyl alcohol, by stirring with a high-intensity stirrer. A paper is gravure-printed with this printing ink and the resulting print is transferred to a fabric as described above. A comparably good result is obtained.

If the abovementioned dyestuff is replaced by other dyestuffs suitable for transfer printing, such as are described in British patent specification No. 1,221,126, comparably good results are obtained.

EXAMPLE 7

40 Parts of dichloroindanthrone are ground in 60 parts of water, with addition of 2 parts of Tamol® NNOK (BASF, Rohm & Haas), and with 200 parts of glass beads of 2 mm diameter as grinding bodies, in a stirred ball mill made of glass, until no particles larger than 1 micron are left in the dispersion.

The dispersion is separated from the grinding bodies, filtered and then stirred thoroughly with a solution of 26.4 parts of Hercules Resin B 106 (Hercules) in 100 parts of sec.-butanol saturated with water. The mixture is then diluted slowly with 200 parts of water and is decanted, the residue is made up with 200 parts of water, stirred and granulated in a Turmix® and again decanted, the residue then obtained is taken up in 400 parts of water and left to stand for one hour, and the granules formed are filtered off, washed with water and dried.

10 Parts of the formulation are sprinkled into 100 parts of a 10% strength solution of ethanolamine in water. A cotton fabric is impregnated with this dispersion on a padder, squeezed off to a weight pick-up of 70% and dried in a hot flue at 100°. It is then impregnated with a solution which contains 3% of sodium hydroxide and 3% of sodium dithionite, squeezed off and steamed for 30 seconds in saturated steam. The dyeing is then rinsed and soaped. A very good dyeing, with an even appearance of the goods, is obtained.

If instead of the abovementioned dyestuff, the same amounts of another vat dyestuff, such as, for example, flavanthrone, 1,5-dibenzoylaminoanthraquinone. C.I. Vat Yellow 1, C.I. Vat Orange 11 or C.I. Vat Brown 33 is used, and in other respects the procedure described above is followed, comparably easily dispersible and applicable formulations are obtained.

EXAMPLE 8

30 parts of copper phthalocyanine are ground in 100 parts of sec.-butanol saturated with water, as described in Example 2. 30 Parts of Hercules Resin B 106 (Hercules) are stirred into this dispersion, after which the dispersion is diluted with water until fine granules have formed; these are stirred with water, filtered off, washed and dried. The formulation, when stirred into a viscose spinning composition and spun, gives an excellent blue dyeing.

EXAMPLE 9

50 Parts of indanthrone in 50 parts of water are ground, with addition of 1 part of dinaphthylmethanedisulphonate, to a mean particle size of 1 micron by means of 200 parts of glass beads. The resulting dispersion is separated from the beads, filtered and stirred with 10 parts of a solution of SMAC A (Van Baerle) in methyl ethyl ketone saturated with water, and water is then added gradually until the formulation has assumed a finely granular form. The aqueous phase is filtered off and the formulation is twice covered with water, then filtered off, washed and dried.

The process of this example is repeated using 5 parts of SMAC A (van Baerle). Highly concentrated formulations are obtained, which can easily be dispersed in water with addition of ammonia. The dispersion can be used for dyeing or printing of textiles in accordance with known vat dyeing processes or for pigmenting of paper or plastics.

I claim:

1. A process for the preparation of aqueous-dispersible, free-flowing, and low-dusting concentrated formulations in powder or granular form of substances which are sparingly soluble to insoluble in water comprising the steps of:
   (i) finely dispersing at least one of said substances, in the organic phase of a two-phase system consisting of water and an organic solvent, said organic solvent having a limited solubility in the aqueous phase,
   (ii) turbulently mixing said two-phase system, containing the substance in the organic phase and having a liquid to paste-like consistency, with at least one organic carrier, said carrier having a molecular weight of at least 500, being sparingly soluble to insoluble in water, containing at least one acid group and being convertible into a water-soluble form with bases, until a homogeneous mixture has been obtained,
   (iii) reducing the volume of the organic phase, said organic phase containing the substance and the carrier, by adding further water until formulation particles consisting of the substance and the carrier are formed and are no longer sticky,
   (iv) separating off said formulation particles, and
   (v) rinsing off with water said separated particles.

2. The process according to claim 1, wherein said substance comprises at least one member selected from the group consisting of water-insoluble dyestuffs, water-insoluble dyestuff precursors, water-insoluble optical brighteners, and pigments.

3. The process according to claim 2, wherein said substance comprises at least one member selected from the group consisting of water-insoluble dyestuffs and optical brighteners.

4. The process according to claim 2, wherein said substance is a water-insoluble dyestuff precursor.

5. The process according to claim 2, wherein said substance is a pigment.

6. The process according to any one of claims 1 to 5, wherein said substance is mechanically comminuted in the two-phase system until it has a particle size of less than 10 microns.

7. The process according to claim 1 wherein said organic solvent has a solubility of at least 1% by weight in the aqueous phase and is selected from the group consisting of an alcohol, a ketone, an aldehyde, an acetal, an ester and an ether.

8. The process according to claim 1 wherein said carrier has a molecular weight of at least 1,000 and is free from synthetic resins which are soluble only in organic media.

9. The process according to claim 8, wherein said carrier is a maleic acid derivative.

10. The process of claim 1 wherein said water phase further contains electrolytes.

11. The process of claim 1, further including the step of drying said rinsed particles.

12. The process of claim 6 wherein said particle size is less than 5 microns.

13. The process of claim 7 wherein said organic solvent has a solubility of at least 10% by weight in the aqueous phase.

14. The process of claim 9 wherein said maleic acid derivative is a styrene/maleate resin having an acid number of at least 50.

15. The process of claim 14 wherein said styrene/maleate resin has an acid number of more than 100.

* * * * *